United States Patent [19]

Davidson et al.

[11] Patent Number: 5,372,660
[45] Date of Patent: Dec. 13, 1994

[54] SURFACE AND NEAR SURFACE HARDENED MEDICAL IMPLANTS

[75] Inventors: James A. Davidson, Germantown; Ajit K. Mishra; Robert A. Poggie, both of Memphis, all of Tenn.

[73] Assignee: Smith & Nephew Richards, Inc., Memphis, Tenn.

[21] Appl. No.: 112,612

[22] Filed: Aug. 26, 1993

[51] Int. Cl.$^5$ ............................................. C22C 14/00
[52] U.S. Cl. ................................. 148/421; 148/669; 420/417; 623/16; 623/18
[58] Field of Search ................. 148/421, 669; 420/417; 623/16, 18

[56] References Cited

U.S. PATENT DOCUMENTS

| | | | |
|---|---|---|---|
| 2,987,352 | 6/1961 | Watson | 308/241 |
| 3,615,885 | 10/1971 | Watson et al. | 148/6.3 |
| 3,643,658 | 2/1972 | Steinemenan | 128/92 D |
| 3,765,954 | 10/1973 | Tokuda et al. | 428/660 |
| 4,040,129 | 8/1977 | Steinemann et al. | 3/1.9 |
| 4,141,759 | 2/1979 | Pfistermeister et al. | 148/6.35 |
| 4,547,228 | 10/1985 | Girrell et al. | 148/16 |
| 4,671,824 | 6/1987 | Haygarth | 148/6.11 |
| 4,687,487 | 8/1987 | Hintermann | 623/18 |
| 4,857,269 | 8/1989 | Wang et al. | 420/417 |
| 5,037,438 | 8/1991 | Davidson | 623/18 |
| 5,169,597 | 12/1992 | Davidson et al. | 428/613 |

OTHER PUBLICATIONS

Thul, R. Med. Prog. Through Tech. 16 (1990)225 Ramoul et al.
Jour-Less Common Metals 99 (1984) 63 Wiedemann et al.
Met. Trans. 18A (1987) 1503.
Streicher, R. M., Weber, H., Schon, R., Semlltsch, M., *Wear Behavior of Different Ceramic Surfaces in Comparison to Tin and ADH-Treated Ti-6A1-7Nb Alloy Paired with Polyethylene*, Paper presented at OIMTEC, Italy (1990).
Streicher, R. M., Weber, H., Schoen, R., Semlitsch, M. F., *Tribological Behaviour of a New Wear Couple: ODH Treated TiA1Nb-Alloy Against UHMWPE*, 7th Meeting of European Soc. of Biomechanics, Denmark, (Jul. 8–11, 1990).

*Primary Examiner*—Upendra Roy
*Attorney, Agent, or Firm*—Pravel, Hewitt, Kimball & Krieger

[57] ABSTRACT

Surface and near surface hardened medical implants are provided. These implants are fabricated from titanium alloys that contain an amount of zirconium sufficient to permit the formation of a significant amount of zirconium oxide at the surface of the implant to cause surface hardening. Further, the zirconium-containing titanium alloy implants are characterized in having an alloy core with an oxygen-rich layer surrounding the core, and a surface layer, overlying the oxygen-rich layer, including mixed oxides of the metals present in the alloy. A zirconium-rich interface may sometimes be present between the oxygen-rich layer and the mixed-oxide surface layer. The method of producing these surface hardened implants includes the steps of heating the implant in an oxygen containing environment at a temperature sufficient to allow oxygen to diffuse to and react with the implant surface and near surface.

24 Claims, 5 Drawing Sheets

SURFACE AND NEAR SURFACE HARDENED MEDICAL IMPLANTS

BACKGROUND OF THE INVENTION

1. Field of the Invention

This invention relates to surface hardened zirconium-containing titanium medical implants, and in particular such hardened implants where the surface and near surface region is comprised of a mixed-oxide surface layer and an underlying near-surface-oxygen-rich solution layer. A zirconium-rich interface develops, in some instances, between the mixed oxide layer and the oxygen-rich solution. In particular, these surface hardened zirconium-containing titanium implants may be produced by an elevated temperature process which permits the diffusion of oxygen into the near surface of the implants. This invention is especially useful for medical implants but is also useful for other applications in which improvement in wear resistance of titanium alloys is beneficial.

2. Description of the Related Art

Titanium alloys are used extensively in medical implants such as hip joint prostheses, knee joint prostheses, spinal implants, bone plate systems, intramedullary nails, dental implants, cardiovascular implants, ear-nose-and-throat implants, etc., due to their high strength, low modulus, excellent biocompatibility and corrosion resistance. However, a major disadvantage of titanium alloys is their susceptibility to wear and galling.

Minimizing wear debris generated by orthopedic devices, such as hip joint and knee joint prostheses, is an issue of concern in orthopedics. Wear debris generated by orthopedic devices has been associated with a phenomenon called "osteolysis," a term used to describe death of bone cells. This can lead to premature loosening of an orthopedic implant from surrounding bone and subsequent failure of the device.

Titanium alloys are also susceptible to a phenomenon called "galling," essentially the sticking together of mating titanium parts which move against each other leading to high friction and wear.

Numerous methods have been proposed for increasing the surface hardness and reducing the wear and galling of titanium alloys. Ceramic coatings, such as titanium nitride, have been deposited on these alloys by processes such as physical vapor deposition and chemical vapor deposition (see, for example, Hintermann, U.S. Pat. No. 4,687,487). However, these ceramic coatings are much harder and stiffer than the base alloy substrate so that there is an abrupt mismatch in the stiffness of the coating and the substrate at the interface between the two. The elastic modulus (stiffness) of a titanium nitride coating is typically about 400 GPa while that of most titanium alloys is about 65 to 130 GPa. This modulus mismatch leads to undesirable stresses at the interface, especially when these components are bent or deformed in any manner, and increases the potential for the coating separating from the substrate by a delamination or spalling mechanism.

Attempts have been made to harden titanium alloys by nitrogen or oxygen ion implantation. In these processes, the titanium alloy substrate is bombarded with nitrogen or oxygen ions using a high voltage apparatus which forces the ions to penetrate the substrate. However, these processes affect the surface to a depth of only about 0.1 micron and peak hardness is not at the surface but slightly below the surface. Hence, the hardened surface tends to wear through relatively quickly.

Titanium alloys have also been hardened by processes such as gas nitriding and salt bath nitriding. These processes also produce a titanium nitride surface on these alloys by penetration of nitrogen into the metal substrate. However, as mentioned above, titanium nitride has a much higher stiffness than the titanium alloy base material, thus being potentially susceptible to detachment from the substrate by delamination or spalling.

There have been a few attempts at oxygen diffusion hardening of titanium alloys, such as for instance disclosed by Streicher, et al., in two conferences (CIMTEC, 1990, Italy, and European Society of Biomechanics, July 8-11, Denmark). However, the alloy used by Streicher, et al., is Ti—6Al—7Nb, which when oxidized would be expected to produce titanium oxide (TiO) or titanium dioxide ($TiO_2$), both of which have very low shear strength and would be susceptible to detachment.

British Patent No. 1351062 discloses a process for surface hardening a titanium article by heating it in an atmosphere of air, nitrogen, hydrogen or oxygen. However, if heated in air, the surface would be expected to consist of titanium oxide (TiO), titanium dioxide ($TiO_2$), or titanium nitride with the associated disadvantages described above. If heated in nitrogen, the surface produced would consist of titanium nitride with the associated stiffness mismatch disadvantage described above. If heated in hydrogen, the compound produced would be titanium hydride which is known to severely embrittle and be detrimental to the fatigue strength of titanium alloys. If heated in oxygen, the surface would be expected to consist of titanium oxide (TiO) or titanium dioxide ($TiO_2$) with the associated low shear strength described above.

Clearly, the development of an effective means for increasing the surface hardness and wear resistance of titanium alloys would be extremely beneficial. In the case of medical implants, abrasive wear may be minimized or eliminated by increasing the hardness of the surface of a titanium alloy. A highly wear resistant titanium implant will not only produce less wear debris which will increase the expected service life of the implant, but will result in reduced levels of metal ion release into the recipient's body tissue. Further, a longer lasting implant may reduce the need for later surgery to replace the implant. Such a process would also be extremely beneficial in reducing wear and galling in non-medical applications of titanium alloys.

SUMMARY OF THE INVENTION

The invention provides novel surface and near-surface hardened implants of titanium alloys containing zirconium. While the titanium alloys may optionally contain other alloying elements, the presence of zirconium is essential. Thus, the alloys are herein referred to as "titanium-zirconium" (Ti—Zr) alloys even though the zirconium content may be quite low and other alloying metals may be present in larger quantity.

The hardened Ti—Zr implants described herein is comprised of a complex oxide film containing mixed Ti and Zr oxides at the implant surface. Immediately underlying this mixed-oxide film is a region of oxygen-rich metal alloy. Underlying the oxygen-rich alloy layer is the core zirconium-containing titanium alloy. The interface between the oxygen rich alloy and the oxide regions may, in some instances, be zirconium-rich in comparison to the underlying zirconium-containing titanium alloy.

An illustrative diagram, not to scale, of a cross section of an invention surface hardened implant is shown in the schematic diagram of FIG. 1. The core zirconium-containing titanium alloy 1 is covered by a layer of oxygen-rich alloy 2 which in turn is covered by the surface layer of mixed-oxides 3. The thin interface 4 shown between the oxygen-rich alloy is not always obtained and is zirconium-rich.

This invention is particularly useful if the hardened core alloy is the Ti—Nb—Zr alloy, described in our co-pending application, U.S. Ser. No. 08/036,414, filed Mar. 24, 1993, which is a related application of U.S. Pat. No. 5,169,597, both of which are hereby incorporated by reference as if fully set forth.

One embodiment of the surface and near surface hardened Ti—Zr implants described herein is comprised of an alloy that includes niobium, a Ti—Nb—Zr alloy, that has a complex oxide surface film, consisting of any or all of $TiO_2$, $Ti_2O_3$, $TiO$, $ZrO_2$, $ZrO$, $NbO$ and $Nb_2O_5$ and several suboxides, at the alloy surface. Underlying this mixed oxide film is a region of oxygen-rich alloy. The interface between the oxygen rich alloy and the mixed oxide regions may be zirconium-rich in comparison to the underlying zirconium-containing titanium alloy.

The surface and near surface hardened zirconium-containing titanium implants described in the current application may be produced by an elevated temperature Oxygen Diffusion Hardening process which significantly hardens the surface and "near surface" of the alloy.

The presence of zirconium in the titanium alloy is required to ensure formation of a mixed oxide surface film containing zirconium dioxide (Zirconia, $ZrO_2$), a ceramic with outstanding attachment to the base alloy and excellent wear resistance. Formation of this ceramic surface by oxidation of zirconium alloys using other processes than herein disclosed, is described in U.S. Pat. Nos. 5,152,794 and 5,037,438, which are hereby incorporated by reference as if fully set forth. The inventions described in the present application are implants of titanium-zirconium alloy with a wear-resistant hardened surface region formed by an oxygen diffusion process.

The mixed-oxide surface film permits the mass transport of oxygen, even at moderate temperatures, into the "near surface" of the metal alloy, underneath the mixed-oxide film. The diffusion of oxygen through the mixed-oxide film into the metal alloy creates a solid solution of the alloy and oxygen, which greatly increases near surface hardness. The deeper this solid solution extends, the thicker the hard surface. However, to obtain thicker solution layers, the implant must be subjected to heat treatment for longer periods of time and this longer heat treatment reduces fatigue strength. Consequently, to maintain fatigue strength, it is preferred that the implant only be heated to produce an oxygen solid solution layer that is less than about 50 microns thick, and more preferably less than about 20 microns thick.

The diffusion hardening process of the invention can be performed over a broad range of temperatures, but preferably between 200° C. and 1200° C. The amount of time required at a given temperature to effectively produce the surface and near surface hardened Ti—Zr alloy is related exponentially, by an Arhennius-type relationship, to the temperature, i.e., shorter periods of time are required at higher temperatures for effective diffusion hardening.

The process of the invention requires a supply of oxygen to the Ti—Zr alloys which are being processed, along with exposure to elevated temperatures. The oxygen required for the diffusion hardening process may be supplied by a pure oxygen or oxygen-containing atmosphere, i.e., one that contains oxygen or compounds which are partially composed of oxygen such as $H_2O$ (water or water vapor), $CO_2$ (carbon dioxide), $NO_2$ (Nitrogen dioxide), $SO_2$ (sulfur dioxide), or any other gaseous, liquid or solid compounds capable of disassociation to produce oxygen at elevated temperatures and/or reduced pressures. Inert gases such as argon, helium or nitrogen may be used as a carrier medium for the oxygen-containing compound.

Since it is preferred that the hardened implants of the invention have surfaces that are unscarred or free of random scratch marks, the use of a fluidized bed is not preferred in the invention method.

| A = Ti-16Nb-17Zr | F = Ti-12Nb-13Zr |
|---|---|
| B = Ti-16Nb-13Zr | G = Ti-9Nb-8Zr |
| C = Ti-13Nb-8Zr | H = Ti-17Nb |
| D = Ti-12Nb-17Zr | I = Ti-12Nb |
| E = Ti-10Nb-13Zr | J = Ti-9Nb |

Figure 1:
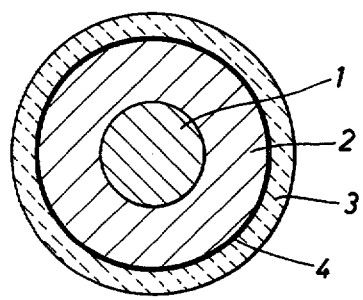
FIG. 1 is an illustrative cross-sectional schematic diagram of a surface and near surface hardened titanium alloy containing zirconium.
Figure 2A:
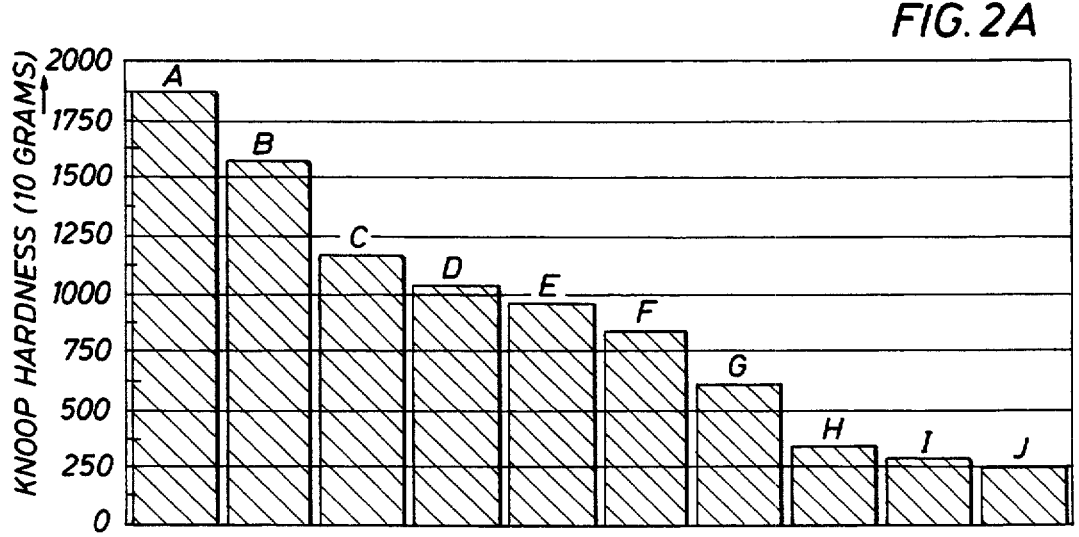
FIG. 2A is a bar graph comparing the Knoop hardness values (10 grams) for the surfaces of the invention, produced by aging the Ti—Nb—Zr alloys for 6 hours at 500° C. in an air atmosphere, with other materials which have been aged in the same manner. The alloys and materials are.
Figure 2B:
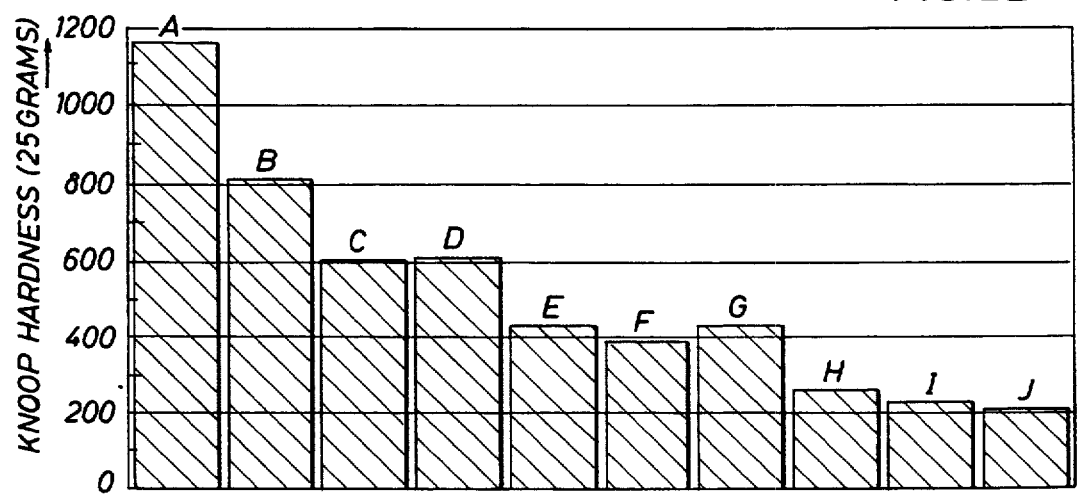

FIG. 2B is a bar graph comparing the Knoop hardness values (25 grams) for the surfaces of the invention, produced by aging Ti—Nb—Zr alloys for 6 hours at 500° C. in an air atmosphere, with other materials which have been aged in the same manner. The key to identify alloys and materials is as for FIG. 2A.

Figure 2C:
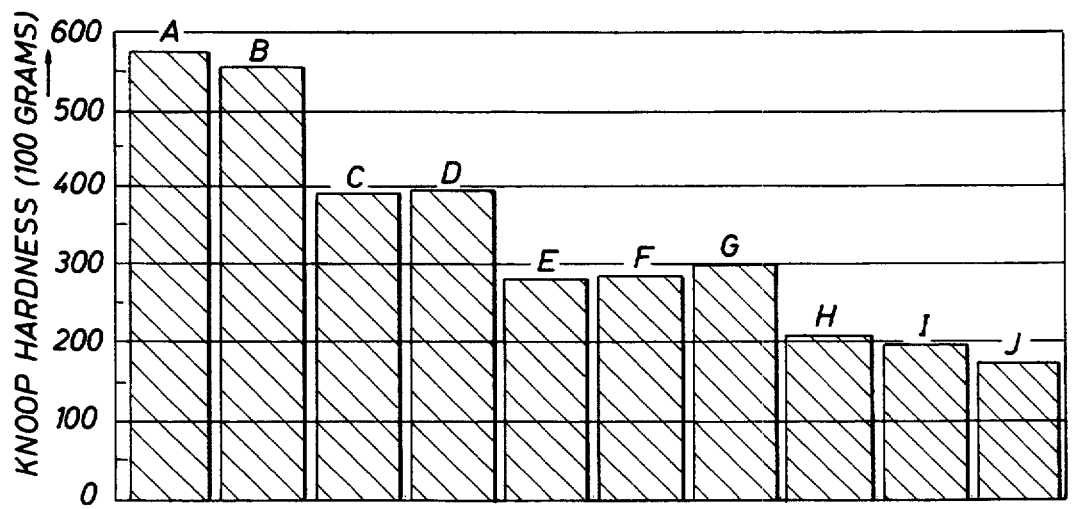

FIG. 2C is a bar graph comparing the Knoop hardness values (100 grams) for the surfaces of the invention, produced by aging Ti—Nb—Zr alloys for 6 hours at 500° C. in an air atmosphere, with other materials which have been aged in the same manner. The key to identify alloys and materials is as for FIG. 2A.

Figure 3A:
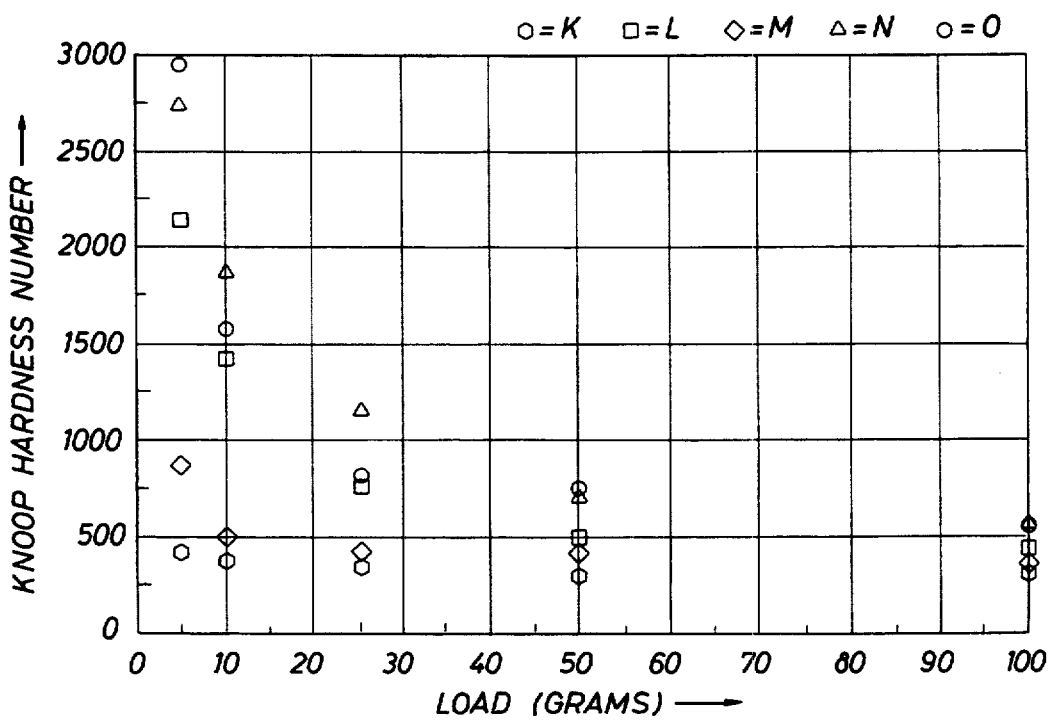
Figure 3B:
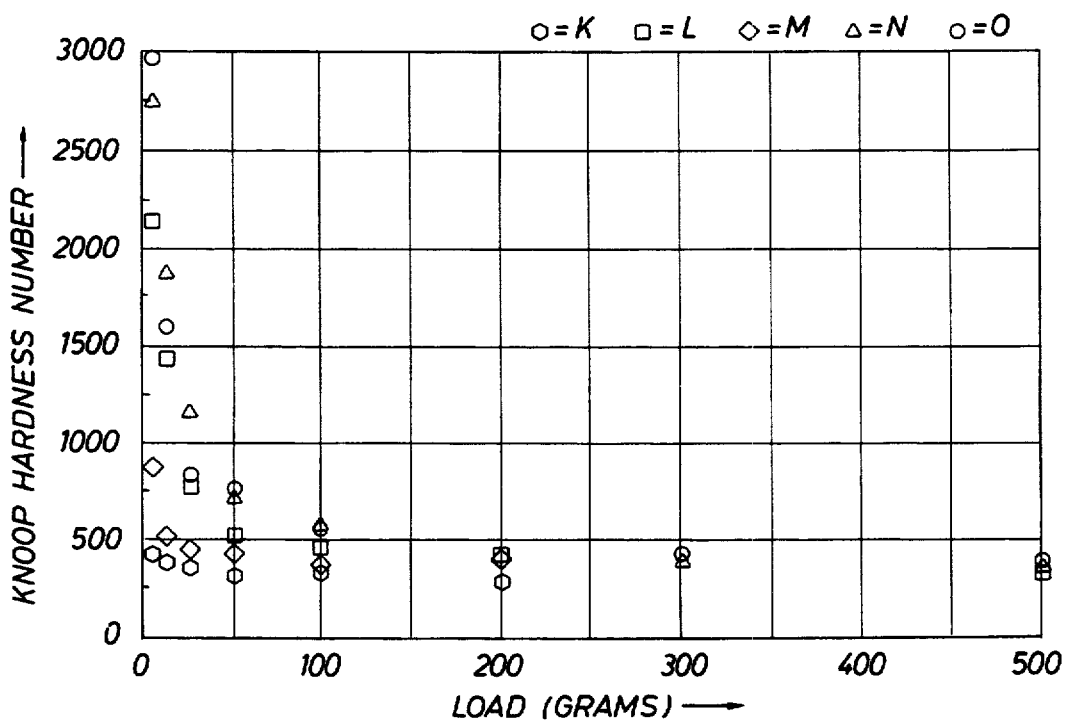

FIG. 3A is a bar graph comparing the Knoop hardness values as a function of load (5-100 grams) of several alloys of the invention with other materials. In FIGS. 3A-B, the alloys of the invention and the other materials are identified as follows:

K = non-hardened Ti—13Nb—13Zr
L = hardened Ti—13Nb—13Zr
M = hardened Ti—6Al—4V
N = hardened Ti—16Nb—17Zr
O = hardened Ti—16Nb—13Zr FIG. 3B is a bar graph comparing the Knoop hardness values as a function of load (5-500 grams) of several alloys of the invention with other materials. The key to identify the alloys and other materials is as for FIG. 3A.

Figure 4A:
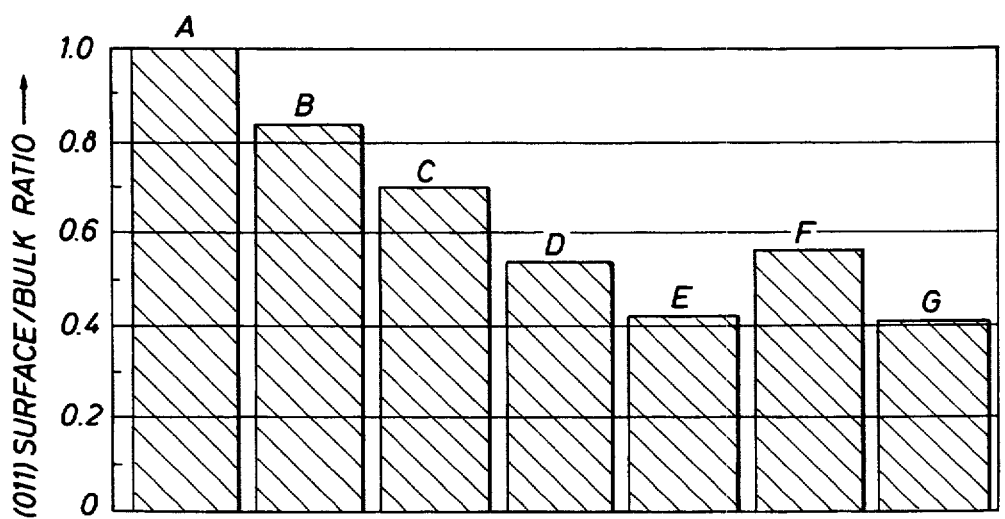

FIG. 4A is a bar graph comparing the ratio for the (011) reflection for the expanded Alpha HCP structure in the near surface to the Alpha HCP structure of the bulk alloy, for several surface hardened alloys of the invention produced by aging the core alloys for 6 hours at 500° C. in an air atmosphere. The alloys are identifiable by the same key for alloys A–G given in the description of FIG. 2A.

Figure 4B:
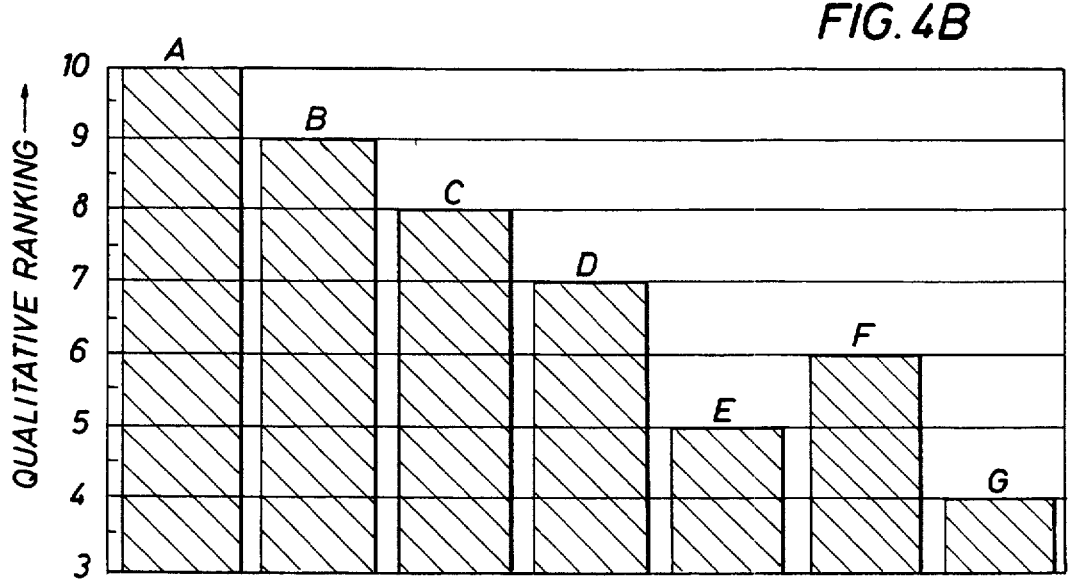

FIG. 4B is a bar graph comparing a qualitative ranking of the lattice distortion observed for the (002) and (001) reflections for several alloys of the invention produced by aging the core alloys for 6 hours at 500° C. in an air atmosphere. The alloys are identifiable by the same key for alloys A–G given in the description of FIG. 2A.

Figure 5:
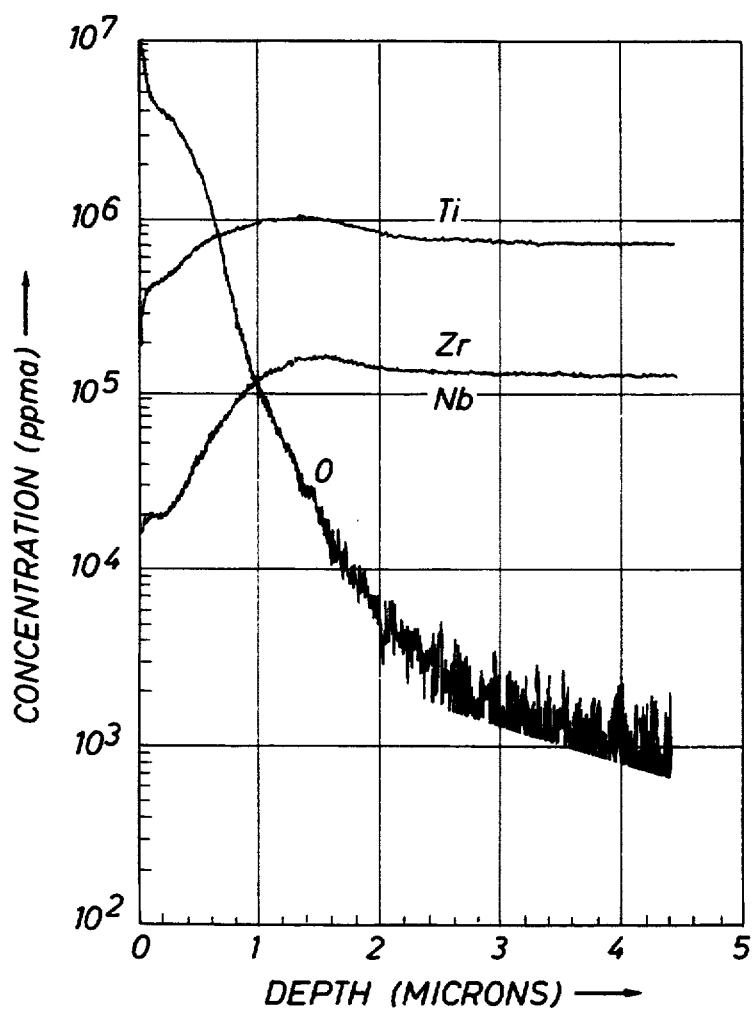

FIG. 5 is an oxygen concentration versus depth curve for the invention produced by subjecting Ti—13Nb—13Zr alloy to a diffusion hardening process including heating up from room temperature to 500° C. in 2.5 hours, a 6 hour soak at 500° C., and cooling to room temperature in 10 hours.

Figure 6:
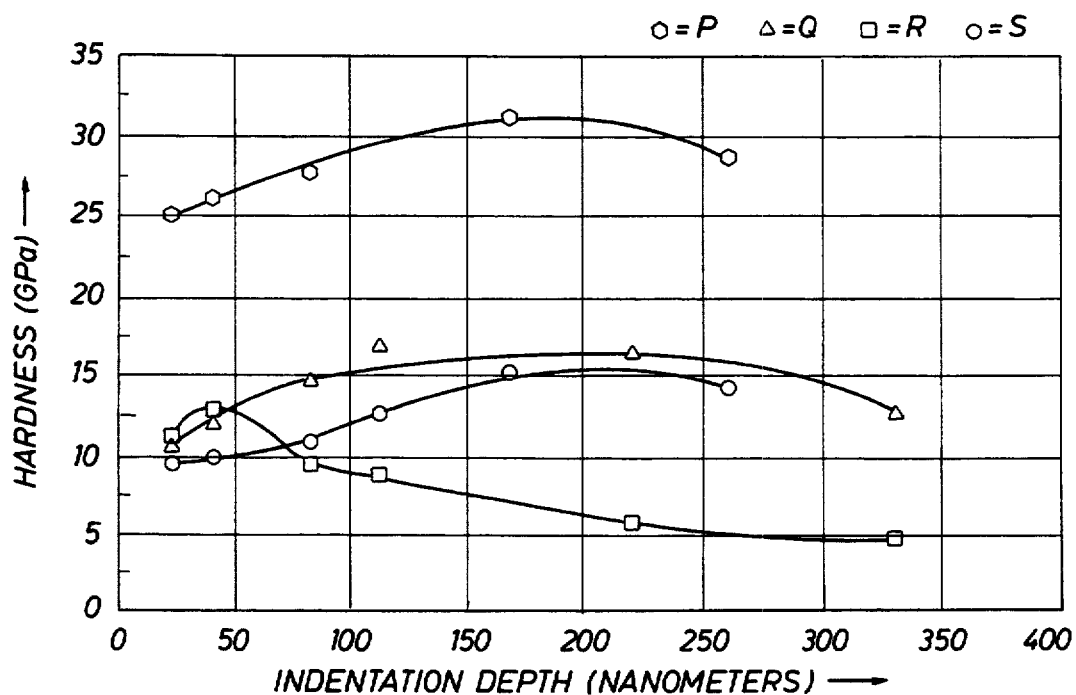
Figure 7:
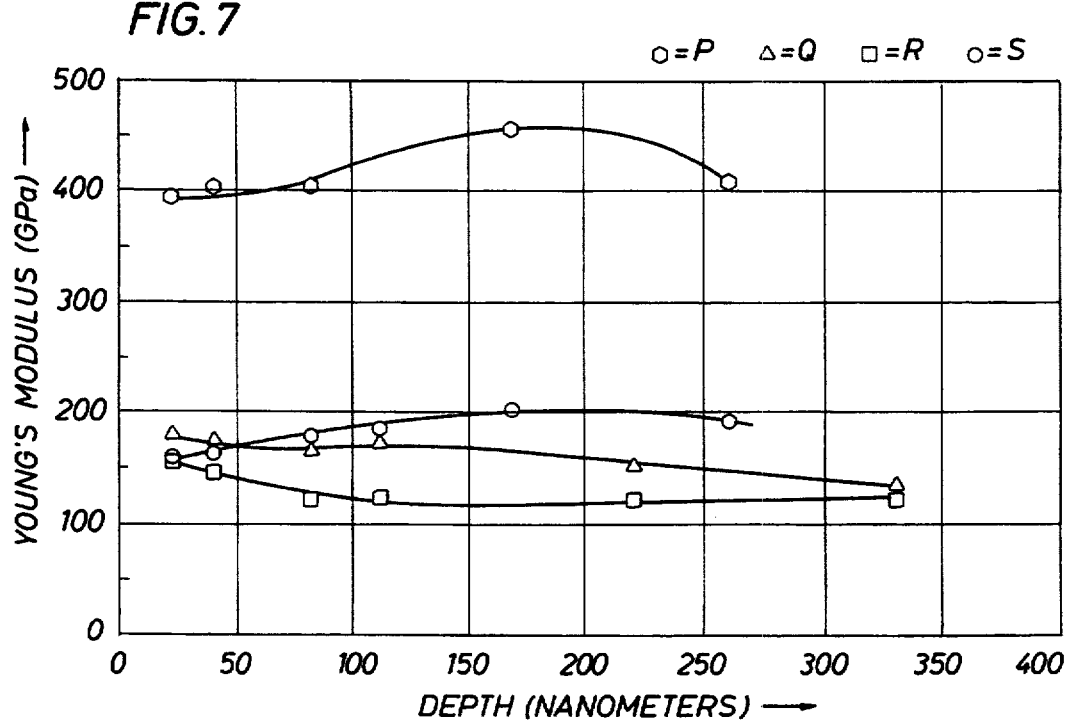

FIG. 6 shows the near surface hardness (measured by Nano Indentor) for the surface and near surface hardened Ti—13Nb—13Zr alloys of the invention and several other processed materials. The alloys and materials may be identified as follows:

P = titanium nitride
Q = oxygen surface hardened Ti—13Nb—13Zr
R = ion-implanted Ti—6Al—4V
S = zirconium oxide FIG. 7 shows the modulus of elasticity (stiffness) as a function of depth for the surface and near surface hardened Ti—13Nb—13Zr alloys of the invention and several other processed materials. The alloys and materials are identifiable by the same key for alloys P—S given in the description of FIG. 6.

DETAILED DESCRIPTION OF THE PREFERRED EMBODIMENTS

While not wishing to be bound by any theory, the inventors offer the following explanation of the invention. The inventors believe that the oxidation of metals and metal alloys (such as the oxygen diffusion hardening process preferred to produce the invention) occurs by one of two primary mechanisms: p-type and n-type oxidations. N-type occurs by the diffusion of oxygen anions into the metal and p-type occurs by the diffusion of metal cations outwards towards the surface (oxygen bearing environment). Iron and copper are classic examples of p-type oxidation while titanium, zirconium and aluminum are examples of n-type oxidation. The oxidation of all metals is facilitated by the presence of crystal lattice defects which promote the movement of both anions and cations through the metallic and oxide crystal lattices.

The oxygen diffusion hardening process preferred for production of the invention implants occurs by diffusion of oxygen into the preferred zirconium-containing titanium alloy to significant depths below the implant's surface (1–50 micron depending on the time, temperature and Zr content). Titanium alloys which do not contain zirconium will be penetrated by oxygen to much smaller depths at comparable temperatures for comparable heating times. These titanium oxide layers are not tightly adherent and therefore not useful in implants.

The presence of zirconium in titanium greatly increases the rate of diffusion of oxygen through the surface mixed oxide into the underlying substrate, by orders of magnitude. This occurs due to the increased number of defects within the oxide lattice caused by the presence of zirconium which permits the exchange of oxygen from the oxygen-rich environment into the oxygen-deficient metal alloy. In addition, zirconium is a highly oxygen-active element and, as such, may tend to segregate to the very surface of a polished, unoxidized surface and at the oxide-metal interface.

The invention provides useful implants of all kinds, including but not limited to hip joint stems, femoral heads, knee femoral components, knee tibial components, bone plates, fixation screws, intramedullary nails, inner ear vent tubes, spinal plates, spinal disks, pelvic plates, dental implants, cardiovascular implants, and compression hip screws.

The preferred diffusion hardening process can be performed by subjecting the implant to a sufficiently high temperature in the presence of oxygen for a time sufficient to form the hardened surface. Temperatures may preferably range from between about 200° C. and about 1200° C. more preferably between about 200° and 700° C., most preferably about 500° C. The amount of time required at a given temperature to effectively harden a Ti—Zr alloy depends upon the temperature used, i.e., shorter periods of time are required at higher temperatures.

The oxygen required may be supplied by an environment containing oxygen or an environment able to provide oxygen under the thermal conditions of oxidation. Thus, the environments include pure oxygen or an oxygen-containing atmosphere, i.e., containing oxygen or compounds which are partially composed of oxygen such as $H_2O$ (water or water vapor), $CO_2$ (carbon dioxide), $NO_2$ (nitrogen dioxide), $SO_2$ (sulfur dioxide), or any other gaseous, liquid or solid compounds capable of dissociation to produce oxygen at elevated temperatures. Inert gases such as argon, helium or nitrogen may be used as a carrier medium for oxygen or oxygen-bearing compounds.

In the most preferred embodiment, the furnace may be purged with argon to remove oxygen. This elimination of oxygen minimizes the amount of molecular oxygen present and allows the formation of thicker coatings with atomic oxygen formed from the disassociation of an oxygen-containing compound, such as water vapor, and the like. But if thinner hardened layers are desired, then some molecular oxygen is desirably present in the furnace. In the preferred method of the invention, the surface layers of the hardened titanium alloy are produced by a diffusion hardening process using argon as the carrier gas. This carrier gas is most preferably bubbled through a water bath in order to saturate it with water prior to continuous introduction into the diffusion hardening furnace containing the Ti—Zr alloy implant to be surface hardened. As the temperature of the water vapor increases in the furnace, the water vapor dissociates at the implant surface to produce atomic oxygen which diffuses into the titanium-zirconium implant being treated, to produce a hardened surface. The extent of dissociation of water vapor increases with increasing temperature.

The hardened surface preferably has a mixed oxide layer in the range from about 0.1 to about 10 microns thick. Preferably, the oxygen-rich layer is from about 1 to about 50 microns thick.

This diffusion process employed to produce the invention may be carried out at atmospheric pressure. It may also be carried out at a reduced pressure to facilitate generation of oxygen from oxygen-containing compounds such as $H_2O$ (water or water vapor), $CO_2$ (carbon dioxide), $NO_2$ (nitrogen dioxide), $SO_2$ (sulfur dioxide) etc. Diffusion into the implants may also be facilitated by use of high pressures, in combination with elevated temperatures. The most preferred range of pressures for this process is from about $10^{-6}$ torr to about $7.6 \times 10^6$ torr.

A particularly preferred embodiment of the invention is surface hardened Ti—Nb—Zr alloys. The most preferred embodiment is surface hardened Ti—13Nb—13Zr alloy as described in our U.S. Pat. No. 5,169,597 incorporated by reference.

The most preferred temperature cycle used for producing the diffusion hardened implants of Ti—13Nb—13Zr includes subjecting to an oxygen environment preferably created by an inert gas carrying water vapor (as described above); heating from room temperature to about 500° C. in about 2.5 hours; soaking for about 6 hours at about 500° C.; then cooling to room temperature in 1–10 hours; and removing from the oxygen environment.

The following examples serve solely as illustrations of the invention as described above and claimed below and are not intended to limit the scope of the invention in any way.

EXAMPLE 1

A series of surface and near surface hardened Ti—Nb—Zr alloys were produced through diffusion hardening in an air atmosphere. The thermal cycle consisted of a ramp up from room temperature to 500° C. in 2.5 hours, a 6 hour soak at 500° C. and air cooling to room temperature. FIGS. 2A, 2B and 2C contain Knoop micro-hardness values showing that near surface hardness increases with zirconium content of the alloy. The titanium alloys which did not contain zirconium were not diffusion hardened. FIGS. 3A and 3B are plots of Knoop hardness values for Ti—13Nb—13Zr, Ti—16Nb—17Zr, Ti—16Nb—13Zr and Ti—6Al—4V after the diffusion hardening process and of Ti—13Nb—13Zr without diffusion hardening. These two plots show that surface hardness of Ti—6Al—4V (a commonly used FDA-approved implant material) was not affected by the diffusion hardening process at this temperature. This is due to the absence of zirconium. The titanium alloys according to the invention, which contain zirconium, showed improved surface hardness after being subjected to the diffusion hardening process.

EXAMPLE 2

Surface hardened Ti—13Nb—13Zr discs were produced in an atmosphere containing argon, oxygen and water vapor. The diffusion hardening process was performed in an argon/oxygen/water vapor mixed atmosphere during a cycle including increasing temperature from room temperature to 500° C. in 2.5 hours, soaking at 500° C. for 6 hours, and cooling to room temperature in 10 hours. These specimens were subjected to sliding wear against hemispherical pins of polymethylmethacrylate (PMMA), a material which is commonly used as bone cement for the fixation of orthopedic implants to the bone.

The results, given in Table 1, show that invention surface and near surface hardened Ti—13Nb—13Zr disc are several orders of magnitude more wear resistant than Ti—6Al—4V or Ti—13Nb—13Zr.

TABLE 1

| Material | Wear Track Depth ($\mu$m) |
|---|---|
| Ti-6Al-4V | 21 ± 9 |
| Nitrogen ion implanted Ti-6Al-4V | 17 ± 10 |
| Non-diffusion-hardened Ti-13Nb-13Zr | 21 ± 6 |
| Diffusion hardened Ti-13Nb-13Zr | 0.15 ± 0.01 |
| ASTM F-799 Co-Cr-Mo | 0.8 ± 0.2 |

EXAMPLE 3

Surface and near surface hardened Ti—Nb—Zr alloys were produced by subjecting the core alloys to a diffusion hardening process in an air atmosphere. The diffusion hardening process was performed in air under a heating cycle including increasing temperature from room temperature to 500° C. in 2.5 hours, soaking at 500° C. for 6 hours, and air cooling to room temperature. These specimens were analyzed by x-ray diffraction. FIGS. 4A and 4B are bar graphs resulting from analysis of x-ray diffraction data. FIG. 4A ranks the amount of near surface crystal lattice distortion for seven Ti—Zr—Nb alloys. The increase in surface hardness is caused by lattice distortion due to the presence of oxygen in solid solution in the near surface. Lattice distortion is a measure of the effectiveness (the amount of oxygen in solid solution) of the diffusion hardening process. FIG. 4B ranks the same seven alloys based on a qualitative comparison of the x-ray diffraction profiles. Inspection of FIGS. 4A and 4B show them to be in excellent agreement—the hardening effect increases with zirconium content of the alloy.

EXAMPLE 4

Surface and near surface hardened Ti—13Nb—13Zr alloy discs were produced by subjecting the core alloy to diffusion hardening in an atmosphere consisting of argon, oxygen and water vapor. The diffusion hardening process was performed during a thermal cycle including heating from room temperature to 500° C. in 2.5 hours, soaking at 500° C. for 6 hours, and cooling to room temperature in 10 hours. These specimens were analyzed using secondary ion mass spectrometry (SIMS). FIG. 5 is the oxygen profile obtained by SIMS, showing significant oxygen penetration of a depth of 2–3 microns below the surface.

EXAMPLE 5

Surface and near surface hardened Ti—13Nb—13Zr discs were prepared in an atmosphere consisting of argon, oxygen and water vapor. The diffusion hardening process was performed during a cycle including heating from room temperature to 500° C. in 2.5 hours, soaking at 500° C. for 6 hours, and cooling to room temperature in 10 hours. These specimens were analyzed using x-ray photoelectron spectrometry (XPS). Table 2 contains the surface chemistry data collected using XPS, showing that the surface oxide is a mixture of ZrO, $ZrO_2$, $TiO_2$, TiO, $Ti_2O_3$, NbO and $Nb_2O_5$ and several suboxides. This mixed oxide structure provides for a dense, adherent oxide layer which enhances the abrasion resistance of the material. The XPS analyses also showed significant concentrations of oxygen in solid solution within the near surface of the Ti—13Nb—13Zr alloy.

TABLE 2

| Depth (Å) | $TiO_2/TiO_{2-x}$ | TiO | $TiO_{1-x}$ | $Nb_2O_5$ | NbO | $Nb_{1-x}/Nb$ | $ZrO_2$ | $ZrO_{2-x}$ | Zr |
|---|---|---|---|---|---|---|---|---|---|
| 50 | 84% | 0 | 0 | 2% | 0 | 0 | 14% | 0 | 0 |
| 500 | 39% | 4% | 23% | 3% | 4% | 9% | 15% | 2% | 0 |
| 1000 | 25% | 22% | 29% | 2% | 3% | 9% | 7% | 2% | 2% |
| 2500 | 20% | 25% | 36% | 2% | 4% | 9% | 3% | 3% | 3% |

EXAMPLE 6

Surface and near surface hardened Ti—13Nb—13Zr discs were prepared by diffusion hardening in an atmosphere consisting of argon, oxygen and water vapor. The diffusion hardening process was performed during a thermal cycle including heating from room temperature to 500° C. in 2.5 hours, soaking at 500° C. for 6 hours, and cooling to room temperature in 10 hours. These specimens were analyzed using a Nano Indentor and compared with a titanium nitride coating. FIG. 6 contains the surface hardness data obtained using the Nano Indentor for zirconium dioxide and titanium nitride coatings, surface and near surface hardened Ti—13Nb—13Zr (produced by the method described above) and nitrogen ion implanted Ti—6Al—4V. FIG. 6 shows that the hardness of the near surface of diffusion hardened Ti—13Nb—13Zr is comparable to that of ceramic coatings such as titanium nitride and zirconium dioxide. This again demonstrates the exceptionally high hardness of the surface and near surface hardened Ti—13Nb—13Zr. High hardness values are also achievable in other titanium alloys which contain sufficient zirconium as shown in FIGS. 2A, 2B and 2C.

FIG. 7 shows the elastic modulus (stiffness), also obtained by Nano Indentation, of the hardened surface alloys produced by the diffusion hardening process, in comparison to that of zirconium dioxide and titanium nitride coatings. As seen from the figure, the modulus of the titanium nitride coating is significantly higher than that of the other two surfaces, thus producing a greater stiffness mismatch with resultant undesirable stresses at the interface.

Although the invention has been described with reference to its preferred embodiments, those of ordinary skill in the art may, upon reading this disclosure, appreciate changes and modifications which may be made and which do not depart from the scope and spirit of the invention as described above and claimed below.

What is claimed is:

1. A surface and near surface hardened implant of titanium alloys containing zirconium, comprising:
   (a) a zirconium-containing titanium alloy core;
   (b) a layer, surrounding the core, of oxygen-rich alloy solution; and
   (c) a surface layer, overlying the oxygen-rich alloy layer, of mixed oxides of metals present in the alloy core.

2. The surface and near surface hardened implant of claim 1, wherein the layer of oxygen-rich alloy solution and surface layer of mixed oxides are formed by subjecting the zirconium-containing titanium alloy core to elevated temperatures in an environment able to provide oxygen and from which oxygen can diffuse into the surface of the alloy.

3. The surface and near surface hardened implant of claims 1 or 2, wherein said layer of oxygen-rich alloy is less than about 50 microns thick.

4. The surface and near surface hardened zirconium containing implant of claim 1, wherein the layers are formed at temperatures between about 200° C. and about 1200° C.

5. The implant of claim 1, wherein the heating is up to from about 200° to about 700° C.

6. The surface and near surface hardened zirconium containing implant of claim 2, further comprising a zirconium-rich interface between the oxygen-rich layer and the mixed-oxide surface layer.

7. The surface and near surface hardened zirconium containing implant of claim 2, wherein the layers are formed in an environment comprising oxygen-containing compounds which are partially composed of oxygen and that disassociate to produce oxygen at temperatures at which the layers form.

8. The surface and near surface hardened zirconium containing implant of claim 2, wherein the titanium alloy comprises:
   titanium; from about 10 wt. % to about 20 wt. % niobium; and from about 0.5 wt. % to about 20 wt. % zirconium.

9. The surface and near surface hardened zirconium containing implant of claim 2, wherein the core metallic alloy comprises:
   titanium; from about 35 wt. % to about 50 wt. % niobium; and from about 0.5 wt. % to about 20 wt. % zirconium.

10. The surface and near surface hardened zirconium containing implant of claim 2, wherein the core metallic alloy comprises:
    about 74 wt. % titanium; about 13 wt. % niobium; and about 13 wt. % zirconium.

11. The surface and near surface hardened zirconium containing implant of claim 2, wherein the layers and interface are formed by a process comprising:
    (a) exposing the implant to an oxygen-containing environment;
    (b) heating the implant up to about 500° C. in about 1 to about 10 hours;
    (c) thermally soaking the heated implant for about 2 to about 8 hours at about 500° C.; and
    (d) cooling the soaked implant to room temperature in about 1 to about 10 hours.

12. The implant of claim 5, wherein the environment comprises argon, oxygen, and water vapor.

13. The implant of claim 5, wherein the environment comprises a composition having chemically bound oxygen that is released for forming an oxide with elemental metal at implant substrate surfaces during the steps of heating and soaking.

14. The surface and near surface hardened zirconium containing implant of claim 7, wherein inert gases are used as a carrier medium for the oxygen-containing compounds.

15. The surface and near surface hardened zirconium containing implant of claim 10, wherein the heating is in a furnace continuously supplied with oxygen-containing gasses.

16. The surface and near surface hardened zirconium containing titanium implant of claims 1 or 2, wherein said layer of oxygen-rich alloy is less than about 20 microns thick.

17. The surface and near surface hardened zirconium containing implant of claims 1 or 2, wherein said surface layer of mixed-oxides is from about 0.1 to about 10 microns thick.

18. A surface hardened medical implant comprising a zirconium-containing titanium alloy, the surface hardened implant produced by a process comprising:
   (a) subjecting zirconium-containing titanium implant substrate to an environment able to provide oxygen;
   (b) heating the zirconium-containing implant substrate to a temperature that allows oxygen to diffuse into surfaces of said implant;
   (c) soaking the zirconium-containing implant substrate at the temperature for a time sufficient to oxidize elemental metal at the surfaces of the implant substrate; and
   (d) producing a hardened medical implant comprising a hard mixed-oxide surface layer on the zirconium-containing implant substrate and an oxygen-rich layer beneath said mixed oxide surface layer.

19. The implant of claim 18, wherein the zirconium-containing titanium alloy is selected from the group of alloys consisting of:
   (i) titanium, about 10 to about 20 wt. % niobium, and about 0.5 to about 20 wt. % zirconium; and
   (ii) titanium, about 35 to about 50 wt. % niobium, and about 0.5 to about 20 wt. % zirconium.

20. The implant of claim 19, wherein the mixed oxide layer is from about 0.1 to about 10 microns thick.

21. The implant of claim 19, wherein the oxygen-rich layer is from about 1 to about 50 microns thick.

22. A medical implant comprising a zirconium-containing core and a hard mixed oxide surface on said core, the implant produced by a process comprising:
   (a) subjecting an implant substrate comprising a zirconium-containing titanium alloy to an environment able to provide oxygen for oxidizing elemental metal at surfaces of the substrate;
   (b) heating the implant substrate in the environment to a temperature from about 200° to about 1200° C.;
   (c) soaking the implant substrate at a temperature that permits oxidizing of elemental metal at substrate surfaces and diffusion of oxygen beneath the substrate surfaces; and
   (d) producing a hard mixed-oxide surface layer on the zirconium-containing implant substrate and an oxygen-rich layer beneath said mixed oxide surface layer.

23. The medical implant of claim 22, wherein the zirconium-containing titanium alloy selected from the group consisting of:
   (i) titanium, about 10 to about 20 wt. % niobium, and about 0.5 to about 20 wt. % zirconium; and
   (ii) titanium, about 35 to about 50 wt. % niobium, and about 0.5 to about 20 wt. % zirconium.

24. The medical implant of claims 22 or 23, wherein the implant is selected from the group consisting of hip joint stems, femoral heads, knee femoral components, knee tibial components, bone plates, fixation screws, intramedullary nails, inner ear vent tubes, spinal plates, spinal disks, pelvic plates, dental implants, cardiovascular implants, and compression hip screws.

* * * * *

UNITED STATES PATENT AND TRADEMARK OFFICE
CERTIFICATE OF CORRECTION

PATENT NO. : 5,372,660
DATED : DEC. 13, 1994
INVENTOR(S) : JAMES A. DAVIDSON, AJIT K. MISHRA, ROBERT A. POGGIE

It is certified that error appears in the above-identified patent and that said Letters Patent is hereby corrected as shown below:

AT COLUMN 10, LINE 12, DELETE "1" AND INSERT -- 18 --.

Signed and Sealed this

Twenty-seventh Day of June, 1995

Attest:

BRUCE LEHMAN

Attesting Officer

Commissioner of Patents and Trademarks